United States Patent
Neftel

(10) Patent No.: US 6,558,343 B1
(45) Date of Patent: May 6, 2003

(54) DEVICE FOR PERITONEAL DIALYSIS AND METHOD FOR USING SAID DEVICE

(75) Inventor: Frédéric Neftel, Lausanne (CH)

(73) Assignee: Debiotech S.A., Lausanne (CH)

( * ) Notice: Subject to any disclaimer, the term of this patent is extended or adjusted under 35 U.S.C. 154(b) by 0 days.

(21) Appl. No.: 09/647,410

(22) PCT Filed: Apr. 1, 1999

(86) PCT No.: PCT/IB99/00559

§ 371 (c)(1),
(2), (4) Date: Sep. 29, 2000

(87) PCT Pub. No.: WO99/51287

PCT Pub. Date: Oct. 14, 1999

(30) Foreign Application Priority Data

Apr. 2, 1998 (CH) .............................................. 0791/98

(51) Int. Cl.[7] .................................................. A61M 1/00
(52) U.S. Cl. .............................. 604/28; 604/27; 604/29
(58) Field of Search ......................... 604/27–33, 65–67, 604/4.01, 6.09; 210/929

(56) References Cited

U.S. PATENT DOCUMENTS

| 4,618,343 A | | 10/1986 | Polaschegg |
| 5,004,459 A | * | 4/1991 | Peabody et al. ............... 604/29 |
| 5,421,823 A | * | 6/1995 | Kamen et al. ............... 210/929 |

FOREIGN PATENT DOCUMENTS

| DE | 33 33 362 | 4/1985 |
| EP | 402505 | 12/1990 |
| EP | 0 498 382 | 8/1992 |

* cited by examiner

Primary Examiner—Timothy L. Maust
(74) Attorney, Agent, or Firm—Wolf, Greenfield & Sacks, P.C.

(57) ABSTRACT

The present invention relates to the treatment of kidney insufficiency and more particularly to a peritoneal dialysis device. The device is adapted to function in tidal peritoneal dialysis (TPD) mode, the device being characterized by the fact that it is provided with a variation system for varying the parameters of dialysate exchange over time. The system is designed in such a manner as to vary the duration between two cycles for exchanging fractions of dialysate.

41 Claims, 3 Drawing Sheets

DEVICE FOR PERITONEAL DIALYSIS AND METHOD FOR USING SAID DEVICE

The present invention relates to the treatment of kidney insufficiency and more particularly to a peritoneal dialysis device.

Peritoneal dialysis uses the peritoneum of the patient as a semi-permeable membrane in order to filter the blood.

During peritoneal dialysis, a sterile aqueous solution (dialysate) is administered into the peritoneal cavity. The cavity is separated from the blood flow by the peritoneum, in particular, so that diffusive and osmotic exchanges can take place between the dialysate and the blood. Those exchanges result in the elimination of harmful substances such as urea, potassium, and creatinine, which are normally excreted by the kidneys. The diffusion of water through the peritoneum during dialysis is called "ultrafiltration", and the volume of water lost by the patient is called "ultrafiltrate".

Originally, peritoneal dialysis was characterized by the fact that a given volume of dialysate was initially introduced into the peritoneal cavity, the diffusive and osmotic exchanges were then allowed to take place during a determined period of time, and finally the entire volume of dialysate was removed in order to be replaced by a new volume of dialysate.

Subsequently, peritoneal dialysis became automated resulting in the automated peritoneal dialysis (APD) method in which a machine administers and removes the dialysate. That type of operation may be performed several times and is known as the continuous cycling peritoneal dialysis (CCPD) method.

Automation enables dialysis to be performed during the night, for example, while the patient is asleep.

Patent application EP 402 505 A (A. Peabody) corresponds to a continuous cycling peritoneal dialysis device. The system is equipped with pressure detectors in order to measure volume of ultrafiltrate. By injecting a glucose solution, the osmolarity is varied directly, thereby enabling exchanges to take place and thus enabling harmful substances to be eliminated. That device which is based on varying the osmotic gradient has turned out to be limited in comparison to tidal dialysis.

In addition, patent application DE 33 33 362 A (Fresenius A. G.) also describes a device based on varying the osmotic gradient. Liquid is removed intermittently, but only to measure the osmotic concentration of the active substance.

Tidal peritoneal dialysis (TPD) is characterized by a series of cycles comprising administering dialysate, pausing, and removing dialysate, but in contrast to the methods described above, the volume of dialysate is not completely renewed at each cycle. Only a fraction of the total volume is renewed on each cycle with the exception of the last stage of the cycle in which the entire volume is removed.

Application WO 95/27520 describes, in particular, a device for peritoneal dialysis. The volume changed remains constant while exchange is taking place and can be about 300 ml, i.e. less than 15% of the volume initially administered.

With such volumes, it is possible to achieve high frequency cycles.

The ability to achieve a high frequency has the advantage of enabling the dialysis to be partially renewed often so as to maintain a better quality dialysate, and thus improved purification of the blood.

Patent application EP 498 382 A (A. Peabody) describes a device that can be used for tidal dialysis. The dialysate exchange parameters do not vary. The frequency and the amplitude of the volumes exchanged are constant, only the residual volume in the cavity increases over time. The observed increase in volume can be described as "accidental" since it is not programmed, and results merely from the increase in ultrafiltrate. Thus, that document does not envisage a system for varying the residual volume.

Although prior-art peritoneal dialysis devices are satisfactory to some extent, some drawbacks still exist, however.

Constantly changing the same volume during treatment results in a high consumption of dialysis liquid and in an increase in treatment duration.

In addition, once the initial volume has been administered, although small volumes are changed periodically, the quality of the dialysate in the peritoneal cavity diminishes over time, thereby degrading purification over time.

The present invention seeks to remedy the above-mentioned drawbacks in particular.

It is characterized by the fact that it is essentially constituted by a device that is provided with a system enabling the dialysate exchange parameters to be varied over time so as to maintain an optimum quality of dialysate, while optimizing the exchange volumes so as to minimize the total consumption of dialysis liquid.

In order to achieve this object, the frequency of the exchange cycles can be varied. It can be low at the start of treatment and increase during treatment as the quality of the dialysate in the peritoneal cavity diminishes.

In addition, the volume changed can vary during treatment. It can be relatively small at the start of treatment and increase during treatment as the quality of the dialysate in the peritoneal cavity diminishes.

The present invention also seeks to vary over time the total volume of dialysate in the peritoneal cavity. For example, the volume can increase during treatment. This scenario can be achieved by administering exchange volumes that are greater than the exchange volumes removed.

The pause period, i.e. the time between the administration of an exchange volume and the removal of an exchange volume, can itself be variable. It can be long at the start of treatment and decrease during treatment so as to compensate, at least in part, for the degradation in blood purification due to the lower quality of the dialysate.

The flowrate during an exchange can be variable. It can be low at the start of treatment and increase over time for the same reasons as mentioned above.

Exchange optimization seeks to obtain improved filtration and more ultrafiltrate while reducing the total volume of dialysate required and the length of the treatment.

The variation system of the device of the invention is programmed by using exchange parameters which are established on the basis of optimization that takes account of the parameters specific to each patient (filtration curves). By way of example, the total volume of diaiysate used, or the length of treatment, can be considered during such optimization.

In particular, it is possible to create mathematical models enabling such optimization to be performed by taking account, amongst other things, of the filtration parameters of the patients under consideration.

It is also possible to warm the liquid for administration to the patient during dialysate exchanges by recovering heat from the dialysate liquid removed from the patient by passing it through a heat exchange system (14). To do this, the liquid removed can, for example, be passed into a tube which, itself, contains another tube for delivering new dialysate liquid to be warmed.

The heat exchange surface area between the two liquids can also be increased by using a coiled tube which passes into a bag containing the liquid that has been removed from the patient.

A system, e.g. of non-return valves, enables the liquid coming from the patient and the liquid going to the patient to be kept separate through the heat excnange system.

Figure 1:
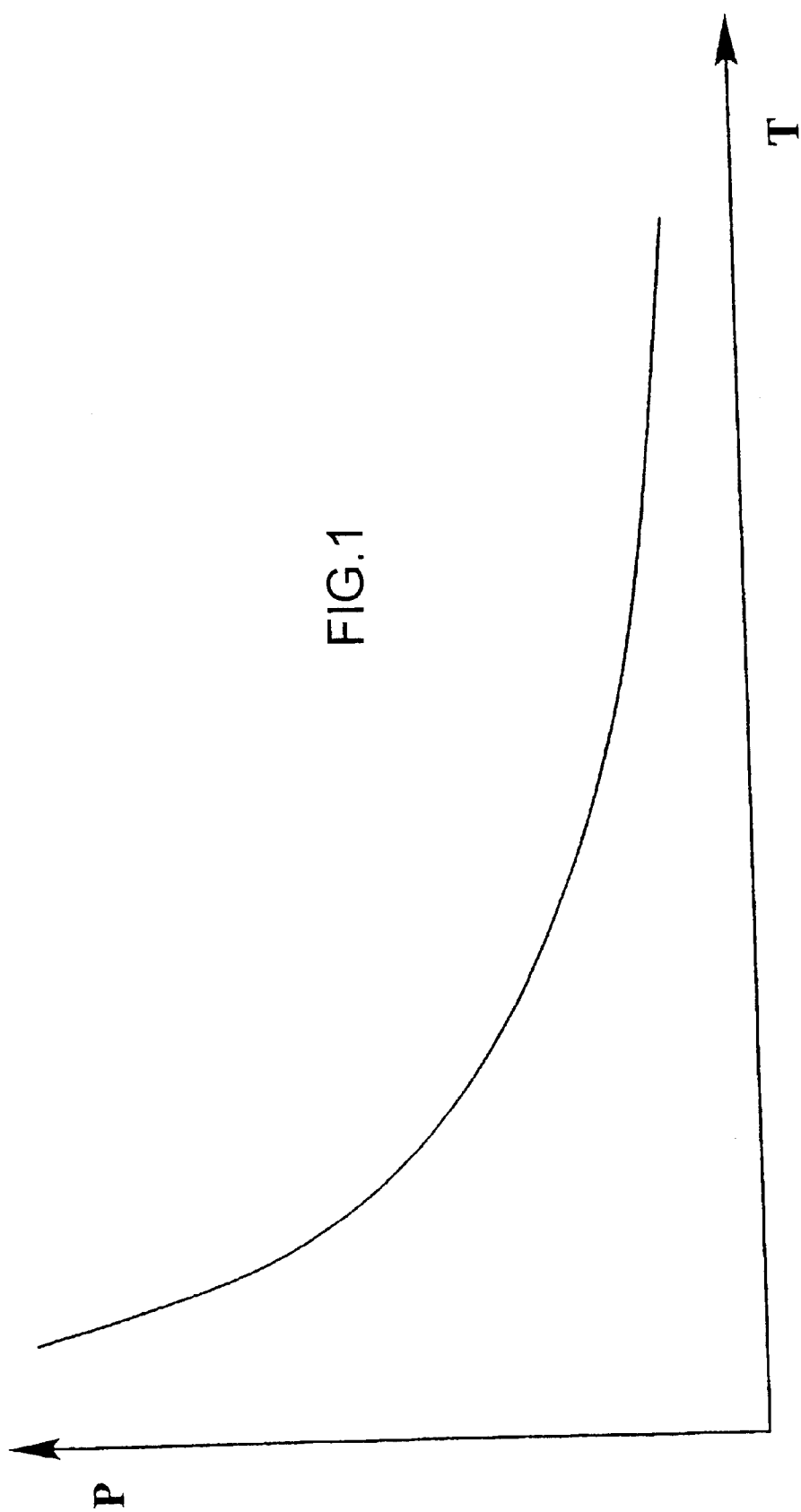
FIG. 1 is a graph showing how purification decreases over time when prior-art devices are used during a cycle.

The graph in FIG. 1 shows purification (Y-axis) as a function of time (X-axis). It can be observed that for an initial volume that is unchanged during treatment, purification degrades exponentially over time.

Figure 2:
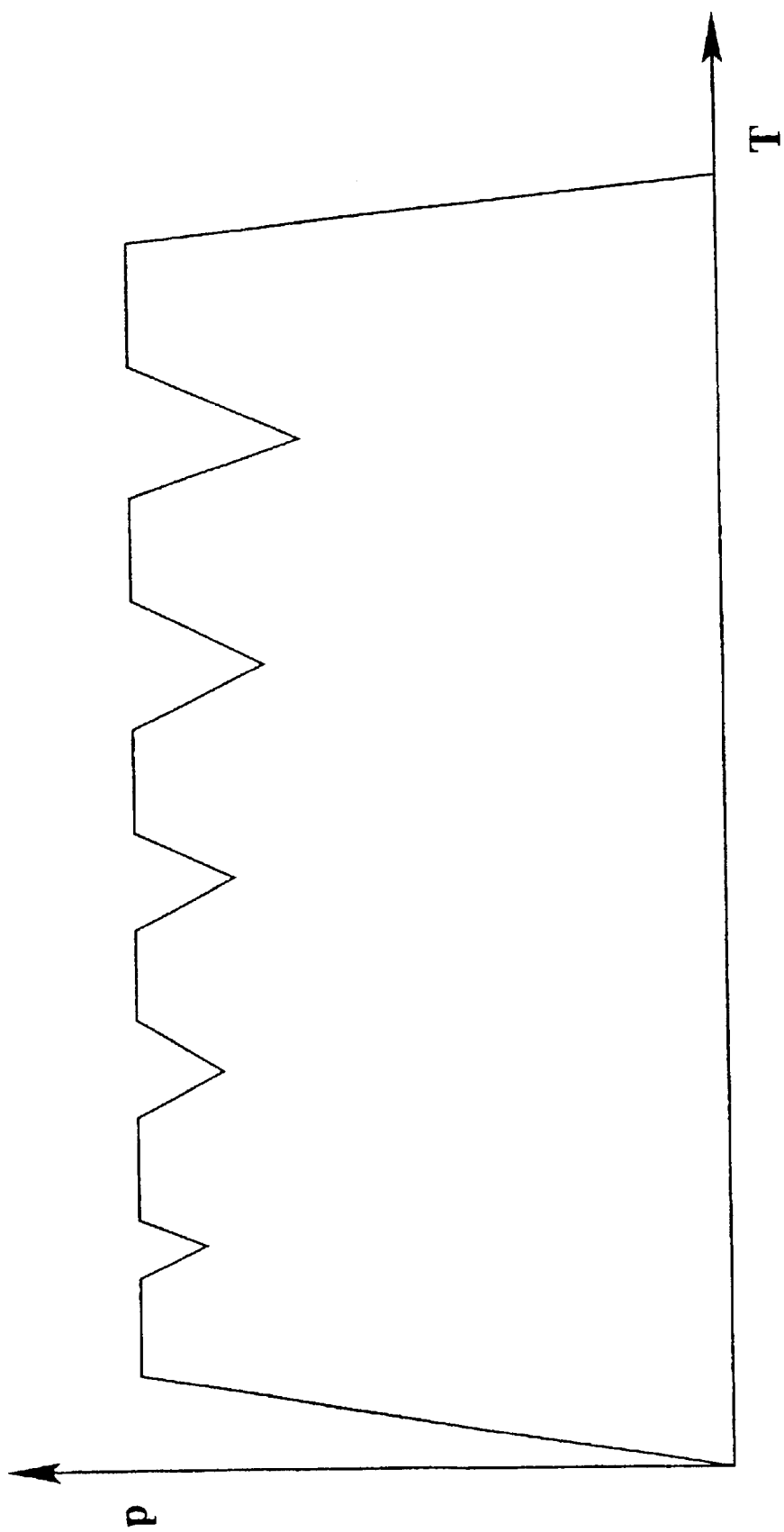
FIG. 2 is a graph showing volume exchanges during treatment in accordance with the present invention.

The graph in FIG. 2 shows the volume of dialysate (Y-axis) in the peritoneal cavity over time (X-axis). In this embodiment, the frequency with which dialysis fractions are exchanged and the volumes of those fractions are both increased over time, thereby causing the degradation in purification shown in graph 1 to be reduced considerably, while optimizing the total quantity of dialysate required.

Figure 3:
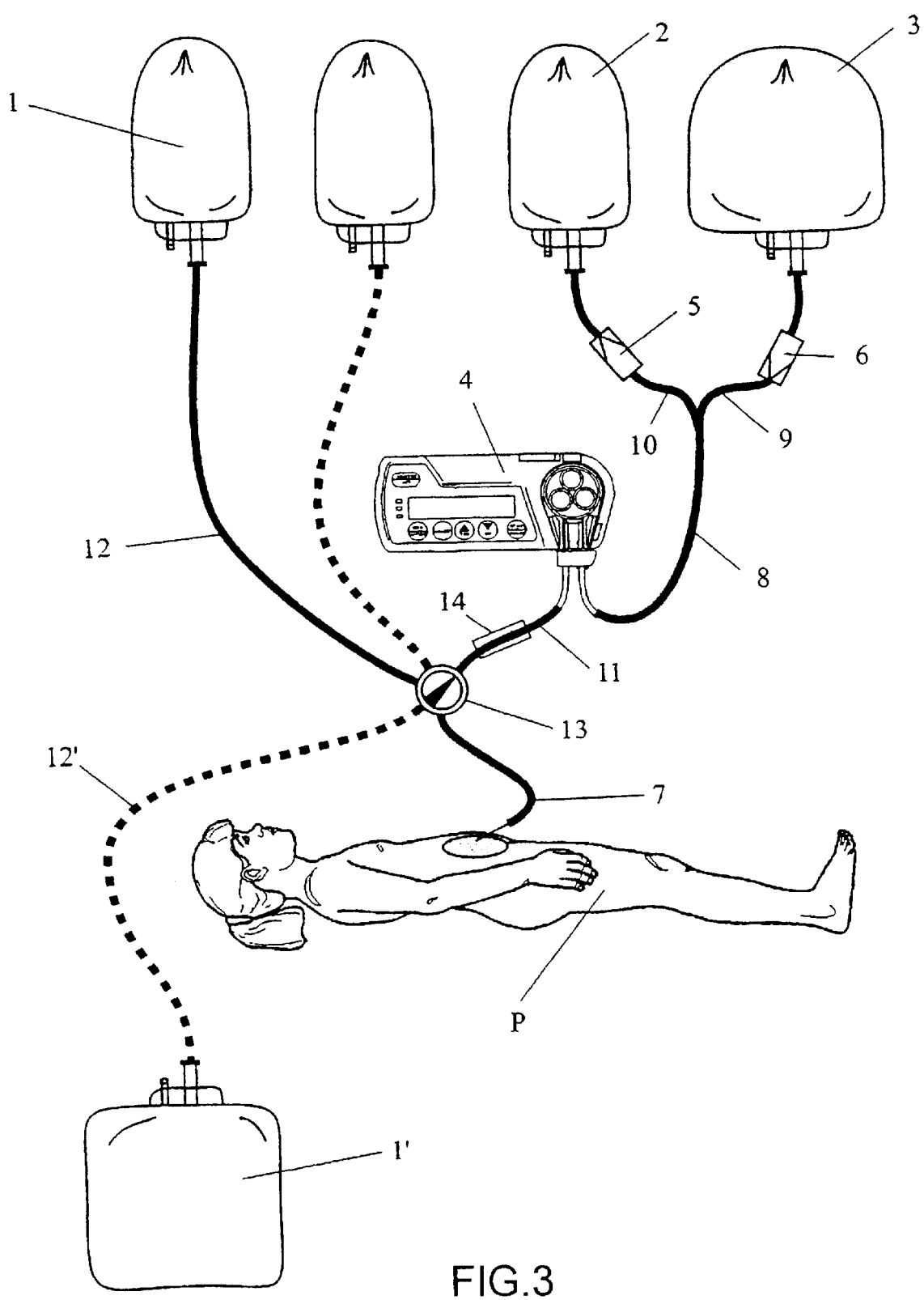
FIG. 3 shows an embodiment of the device of the invention.

The device in FIG. 3 is constituted by a first system of tubes (7, 12) for administering an initial volume which is situated in a first reservoir (1). The same system of tubes, but positioned differently (7, 12'), can be used to recover the volume remaining at the end of treatment.

A second system of tubes (7–11) is provided to administer and remove the exchange volumes. An administration reservoir (3) contains the dialysate to be administered and a recovery reservoir (2) recovers the used dialysate.

The administration reservoir (3) is provided at its outlet with a non-return valve (6) which prevents it from receiving the used dialysate.

The recovery reservoir (2) is provided at its inlet with a non-return valve (5) which prevents the used dialysate from being released accidentally from the recovery reservoir.

The liquid flowing in the second system of tubes is driven by a peristaltic pump (4).

The two systems of tubes are connected together by a multi-port valve (13).

The device of the invention functions in the following manner:

The multi-port valve (13) is disposed in such a manner as to enable the initial volume, which is situated in the first reservoir (1), to be administered to the peritoneal cavity of the patient (P). The first reservoir (1) is disposed in such a manner that the liquid is conveyed by gravity.

Once the peritoneal cavity is full, the multi-port valve (13) is disposed in such a manner as to put the second system of tubes (7–11) into communication with the peritoneal cavity.

During the first volume exchange, the peristaltic pump (4) is actuated in such a manner as to remove an exchange volume. The disposition of the non-return valves (5, 6) enables the used dialysate to be conveyed into the recovery reservoir (2).

Once this step has been performed, the peristaltic pump is actuated in such a manner as to remove an exchange volume from the administration reservoir (3) in order to convey it to the peritoneal cavity.

Such a system can function specifically with a peristaltic pump of low flowrate (of about 2 to 3 liters/hour) such as that described in French patent FR 89 03 234.

This type of operation is performed several times during treatment, while varying the parameters in accordance with the explanations described above.

At the end of treatment, the multi-port valve (13) is disposed in such a manner as to put the first system of tubes (7–12) into communication with the peritoneal cavity. The reservoir (1) is placed in such a manner as to recover the remaining volume by gravity.

It should be noted that the embodiment of the invention described above does not limit the scope of the invention. Any peritoneal dialysis device that varies the parameters for exchanging fractions of dialysate over time must be considered as forming part of the present invention.

What is claimed is:

1. A method of carrying out tidal peritoneal dialysis comprising:

determining, with a variation system, parameters of dialysate exchange based on filtration parameters specific to the patient under consideration, duration and/or volume characteristics of the desired dialysis, and a mathematical model enabling the parameters of dialysate exchange to be calculated in order to optimize the result of dialysis;

based on the determined exchange parameters, administering a series of cycles including administering a fraction of dialysate, pausing, and removing dialysate with a peritoneal dialysis device; and varying, with the variation system, a duration of a cycle from one cycle to another while the peritoneal dialysis device continues to administer cycles in the tidal peritoneal dialysis mode.

2. A method of carrying out tidal peritoneal dialysis comprising:

determining, with a variation system, parameters of dialysate exchange based on filtration parameters specific to the patient under consideration, duration and/or volume characteristics of the desired dialysis, and a mathematical model enabling the parameters of dialysate exchange to be calculated in order to optimize the result of the dialysis;

based on the determined exchange parameters, administering a series of cycles including administering a fraction of dialysate, pausing, and removing dialysate with a peritoneal dialysis device; and varying, with the variation system, a volume of an exchanged dialysate fraction from one cycle to another while the peritoneal dialysis device continues to administer cycles in the tidal peritoneal dialysis mode.

3. A peritoneal dialysis device adapted to function in a tidal peritoneal dialysis mode, the device comprising a variation system for varying the parameters of dialysate exchange over time, said variation system being constructed and adapted to take into account filtration parameters specific to a patient under consideration and to vary a duration of a cycle of exchanging a fraction of dialysate, as compared to a duration of a previous cycle, while functioning in the tidal peritoneal dialysis mode.

4. The device according to claim 3, wherein a cycle includes an administration period, a pause period and a removal period, the variation system being constructed and adapted to vary a duration of the pause period while functioning in the tidal peritoneal dialysis mode.

5. The device according to claim 3, wherein the variation system is constructed and adapted to vary a volume of the exchanged dialysate fraction from one cycle to another while functioning in the tidal peritoneal dialysis mode.

6. The device according to claim 5, wherein the volume administered is not identical to the volume removed in a cycle.

7. The device according to claim 6, wherein the volume administered is less than the volume removed in a cycle.

8. The device according to claim 1, wherein the variation system is constructed and adapted to vary the flowrate of the exchange from one cycle to another.

9. The device according to claim 3, wherein the variation system is constructed and adapted to take account of the total volume of dialysate available over all cycles for a single patient.

10. The device according to claim 3, wherein the variation system is constructed and adapted to take account of the maximum total duration of the dialysis over all cycles for a single patient.

11. The device according to claim 3, further comprising two systems of tubes, a first system of tubes enabling an initial volume to be introduced and removed, and a second system of tubes enabling fractions of dialysate to be exchanged.

12. The device according to claim 11, wherein the liquid in the first system of tubes is conveyed by gravity and the liquid in the second system of tubes is driven by pumping.

13. The device according to claim 11, wherein the second system of tubes is provided with a first reservoir for administering dialysis fractions and with a second reservoir for recovering fractions of dialysate.

14. The device according to claim 13, wherein the first and second reservoirs are each provided with a non-return valve.

15. The device according to claim 11, further comprising a heat exchanger enabling the liquid for administration to be warmed by the liquid that has been removed.

16. The device according to claim 12, further comprising a programmable peristaltic micropump in communication with the second system of tubes.

17. The device according to claim 11, further comprising a multiport valve that is adapted to be actuated automatically by a pump between the first system of tubes and the second system of tubes as a function of the desired exchange cycles.

18. The device according to claim 4, wherein the variation system is adapted to decrease the duration of the pause period.

19. The device according to claim 3, wherein the variation system is adapted to vary the duration of the cycle in the absence of a measurement of chemical composition of the dialysate.

20. A peritoneal dialysis device adapted to function in tidal peritoneal dialysis mode, the device comprising:

a variation system for varying the parameters of dialysate exchange over time, said variation system being adapted to be programmed and established on the basis of optimization that takes account of filtration parameters specific to each patient under consideration, wherein the variation system is adapted to vary a volume of an exchanged dialysate fraction from one cycle to another while functioning in the tidal peritoneal dialysis mode.

21. The device according to claim 20, wherein the volume administered is not identical to the volume removed in a cycle.

22. The device according to claim 21, wherein the volume administered is less than the volume removed in a cycle.

23. The device according to claim 20, wherein the variation system is adapted to be programmed on the basis of the total volume of dialysate available over all cycles for a single patient.

24. The device according to claim 20, wherein the variation system is adapted to be programmed on the basis of the maximum total duration of the dialysis over all cycles for a single patient.

25. The device according to claim 20, further comprising two systems of tubes, a first system of tubes enabling an initial volume to be introduced and removed, and a second system of tubes enabling fractions of dialysate to be exchanged.

26. The device according to claim 25, wherein the liquid in the first system of tubes is conveyed by gravity and the liquid in the second system of tubes is driven by pumping.

27. The device according to claim 26, further comprising a programmable peristaltic micropump in communication with said second system of tubes.

28. The device according to claim 25, wherein the second system of tubes is provided with a first reservoir for administering dialysis fractions and with a second reservoir for recovering fractions of dialysate.

29. The device according to claim 28, wherein the first and second reservoirs are each provided with a non-return valve.

30. The device according to claim 25, further comprising a pump between the first system of tubes and the second system of tubes and a multiport valve which is actuated automatically by the pump as a function of the desired exchange cycles.

31. The device according to claim 20, further comprising a heat exchanger enabling the liquid for administration to be warmed by the liquid that has been removed.

32. The device according to claim 20, wherein the variation system is adapted to increase the volume of the exchanged dialysate fraction from one cycle to another while functioning in the tidal peritoneal dialysis mode.

33. The device according to claim 20, wherein the variation system is adapted to vary the volume of the dialysate fraction in the absence of a measurement of chemical composition of the dialysate.

34. A peritoneal dialysis device adapted to function in a tidal peritoneal dialysis mode by administering a continuous series of cycles, each cycle including administering a fraction of dialysate, pausing, and removing dialysate, the device comprising a variation system programmed with a sequence of instructions defining:

responsive to parameters specific to a patient under consideration and while continuously administering the cycles, varying a duration of a cycle from one cycle to another.

35. The device according to claim 34, wherein varying a duration of the cycle includes varying a duration of the pausing of a cycle.

36. The device according to claim 34, further comprising varying a volume of the fraction of dialysate while administering the continuous series of cycles.

37. The device according to claim 34, further comprising receiving duration and/or volume characteristics of a desired dialysis exchange; and responsive to the parameters specific to each patient and the duration and/or volume characteristics of the desired dialysis, determining the parameters of dialysate exchange to optimize the result of the desired dialysis.

38. The device according to claim 37, wherein varying the duration of the cycle is in the absence of a measurement of chemical composition of the dialysate during a cycle.

39. A peritoneal dialysis device adapted to function in a tidal peritoneal dialysis mode by administering a continuous series of cycles, each cycle including administering a fraction of dialysate, pausing, and removing dialysate, the device comprising a variation system programmed with a sequence of instructions defining:

responsive to parameters specific to a patient under consideration and while continuously administering the cycles, varying a volume of the exchanged fraction of dialysate from one cycle to another.

40. The device according to claim 39, further comprising receiving duration and/or volume characteristics of a desired dialysis exchange; and responsive to the parameters specific to each patient and the duration and/or volume characteristics of the desired dialysis, determining the parameters of dialysate exchange to optimize the result of the desired dialysis.

41. The device according to claim 40, wherein varying the volume of the fraction of dialysate is in the absence of a measurement of chemical composition of the dialysate during a cycle.

* * * * *